United States Patent
Warnaar et al.

(10) Patent No.: US 10,474,043 B2
(45) Date of Patent: Nov. 12, 2019

(54) METHOD OF MEASURING A PROPERTY OF A SUBSTRATE, INSPECTION APPARATUS, LITHOGRAPHIC SYSTEM AND DEVICE MANUFACTURING METHOD

(71) Applicant: ASML Netherlands B.V., Veldhoven (NL)

(72) Inventors: Patrick Warnaar, Tilburg (NL); Maurits Van Der Schaar, Eindhoven (NL); Grzegorz Grzela, Utrecht (NL); Erik Johan Koop, Eindhoven (NL); Victor Emanuel Calado, Rotterdam (NL); Si-Han Zeng, New Taipei (TW)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/841,811

(22) Filed: Dec. 14, 2017

(65) Prior Publication Data

US 2018/0173105 A1 Jun. 21, 2018

(30) Foreign Application Priority Data

Dec. 16, 2016 (EP) .................................. 16204764

(51) Int. Cl.
*G03F 7/20* (2006.01)
*G01N 21/47* (2006.01)
(52) U.S. Cl.
CPC ........... *G03F 7/7065* (2013.01); *G01N 21/47* (2013.01); *G03F 7/70633* (2013.01)

(58) Field of Classification Search
CPC ......... G03F 7/7065; G03F 7/20; G03F 7/7063
(Continued)

(56) References Cited

U.S. PATENT DOCUMENTS 9,140,998 B2 9/2015 Smilde et al.
2004/0246482 A1 12/2004 Sezginer et al.
(Continued)

FOREIGN PATENT DOCUMENTS

WO WO 2013/178422 A1 12/2013

OTHER PUBLICATIONS

International Search Report and Written Opinion of the International Searching Authority directed to related International Application No. PCT/EP2017/080770, dated Feb. 12, 2018; 13 pages.

*Primary Examiner* — Hung Nguyen
(74) *Attorney, Agent, or Firm* — Sterne, Kessler, Goldstein & Fox P.L.L.C.

(57) ABSTRACT

A method of measuring a property of a substrate, the substrate having a plurality of targets formed thereon, the method comprising:
measuring N targets of the plurality of targets using an optical measurement system, where N is an integer greater than 2 and each of said N targets is measured $W_t$ times, where $W_t$ is an integer greater than 2 so as to obtain $N*W_t$ measurement values; and
determining R property values using Q equations and the $N*W_t$ measurement values, where $R<Q \leq N*W_t$;
wherein the optical measurement system has at least one changeable setting and, for each of the N targets, measurement values are obtained using different setting values of at least one changeable setting.

17 Claims, 5 Drawing Sheets

(58) Field of Classification Search
USPC .............................................. 355/52, 53, 55
See application file for complete search history.

(56) References Cited

U.S. PATENT DOCUMENTS

| | | |
|---|---|---|
| 2006/0033921 A1 | 2/2006 | Den Boef et al. |
| 2006/0066855 A1 | 3/2006 | Boef et al. |
| 2006/0073686 A1* | 4/2006 | Zach ..................... G03B 27/72 438/551 |
| 2010/0201963 A1 | 8/2010 | Cramer et al. |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2011/0102753 A1 | 5/2011 | Van De Kerkhof et al. |
| 2012/0044470 A1 | 2/2012 | Smilde et al. |
| 2012/0123581 A1 | 5/2012 | Smilde et al. |
| 2012/0242970 A1 | 9/2012 | Smilde et al. |
| 2013/0128247 A1* | 5/2013 | Khuat Duy ........... G03F 9/7034 355/63 |
| 2013/0258310 A1 | 10/2013 | Smilde et al. |
| 2013/0271740 A1 | 10/2013 | Quintanilha |
| 2016/0161864 A1 | 6/2016 | Middlebrooks et al. |
| 2016/0180517 A1 | 6/2016 | Fuchs et al. |
| 2016/0223322 A1* | 8/2016 | Liu .................... G03F 7/70633 |
| 2016/0313654 A1 | 10/2016 | Zeng et al. |

* cited by examiner

METHOD OF MEASURING A PROPERTY OF A SUBSTRATE, INSPECTION APPARATUS, LITHOGRAPHIC SYSTEM AND DEVICE MANUFACTURING METHOD

This application incorporate by reference in its entirety EP Patent Application No. 16204764, filed Dec. 16, 2016.

BACKGROUND

Field of the Invention

The present invention relates to methods and apparatus for metrology usable, for example, in the manufacture of devices by lithographic techniques, and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. including part of a die, one die, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g. for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g. intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921A1 and US2010201963A1. The targets used by such scatterometers are relatively large gratings, e.g. 40 μm by 40 μm, and the measurement beam generates a spot that is smaller than the grating (i.e., the grating is underfilled). In addition to measurement of feature shapes by reconstruction, diffraction based overlay can be measured using such apparatus, as described in published patent application US2006066855A1. Diffraction-based overlay metrology using dark-field imaging of the diffraction orders enables measurement of overlay and other parameters on smaller targets. These targets can be smaller than the illumination spot and may be surrounded by product structures on a substrate. The intensities from the environment product structures can efficiently be separated from the intensities from the overlay target with the dark-field detection in the image-plane.

Examples of dark field imaging metrology can be found in patent applications US20100328655A1 and US2011069292A1 which documents are hereby incorporated by reference in their entirety. Further developments of the technique have been described in published patent publications US20110027704A, US20110043791A, US2011102753A1, US20120044470A, US20120123581A, US20120242970A1, US20130258310A, US20130271740A and WO2013178422A1. Typically in these methods it is desired to measure asymmetry as a property of the target. Targets can be designed so that measurement of asymmetry can be used to obtain measurement of various performance parameters such as overlay, focus or dose. Asymmetry of the target is measured by detecting differences in intensity between opposite portions of the diffraction spectrum using the scatterometer. For example, the intensities of +1 and −1 diffraction orders may be compared, to obtain a measure of asymmetry.

Measurement accuracy in scatterometry, in particular for overlay measurement, suffers from grating asymmetry disturbances, e.g. asymmetric side wall angle, tilt of the grating floor, due to processing of the target structures. Due to processing differences between locations on the wafer, the effect on the measurement differs from location to location. Furthermore, the sensitivity of the measurement to the grating disturbances depends on the illumination conditions used for the measurement, e.g. wavelength, bandwidth, polarization, aperture shape, etc. Therefore, the accuracy of conventional scatterometry measurements is limited.

SUMMARY OF THE INVENTION

The present invention aims to improve accuracy of measurements in the presence of process variations across a substrate and/or between substrates.

The invention in a first aspect provides a method of measuring a property of a substrate, the substrate having a plurality of targets formed thereon, the method comprising:
measuring N targets of the plurality of targets using an optical measurement system, where N is an integer greater than 2 and each of said N targets is measured $W_t$ times, where $W_t$ is an integer greater than 2 so as to obtain $N*W_t$ measurement values; and
determining R property values using Q equations and the $N*W_t$ measurement values, where $R<Q \leq N*W_t$;
wherein the optical measurement system has at least one changeable setting and, for each of the N targets, measurement values are obtained using different setting values of at least one changeable setting.

The invention in a second aspect provides a device manufacturing method comprising:
forming a first device layer on a substrate, the first device layer including a plurality of targets;
measuring N targets of the plurality of targets using an optical measurement system, where N is an integer greater than 2 and each of said N targets is measured Wt times, where Wt is an integer greater than 2 so as to obtain N*Wt measurement values; and
determining R property values using Q equations and the N*Wt measurement values, where R<Q≤N*Wt;
making a decision about another process step;
wherein the optical measurement system has at least one changeable setting and, for each of the N targets, measurement values are obtained using different setting values of at least one changeable setting; and
the making a decision is based on the R property values.

The invention in a third aspect provides a computer program comprising instructions to cause an optical measurement system to perform a method of measuring a property of a substrate, the substrate having a plurality of targets formed thereon, the method comprising:

measuring N targets of the plurality of targets using an optical measurement system, where N is an integer greater than 2 and each of said N targets is measured $W_t$ times, where $W_t$ is an integer greater than 2 so as to obtain $N*W_t$ measurement values; and determining R property values using Q equations and the $N*W_t$ measurement values, where $R<Q \leq N*W_t$;

wherein the optical measurement system has at least one changeable setting and, for each of the N targets, measurement values are obtained using different setting values of at least one changeable setting.

The invention in a fourth aspect provides an inspection apparatus for measuring a property of a plurality of structures formed by a lithographic process on one or more substrates, the apparatus comprising an illumination optical system, an collection optical system and a processing system, the processing system being arranged to derive a measurement of said property of each structure at least partly from radiation collected by said collection optical system after being scattered by the structure under one or more sets of illumination conditions established by the illumination optical system, the processing system being configured to control the apparatus to derive a measurement of a property of a plurality of structures in the method described above.

The invention in a fifth aspect provides a lithographic system comprising:

a lithographic apparatus comprising:

an illumination optical system arranged to illuminate a pattern;

a projection optical system arranged to project an image of the pattern onto a substrate; and an inspection apparatus as described above, wherein the lithographic apparatus is arranged to use the measurement results from the inspection apparatus, in applying the pattern to further substrates.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Embodiments of the invention will now be described, by way of example, with reference to the accompanying drawings in which.

DETAILED DESCRIPTION

Before describing embodiments of the invention in detail, it is instructive to present an example environment in which embodiments of the present invention may be implemented.

Figure 1:
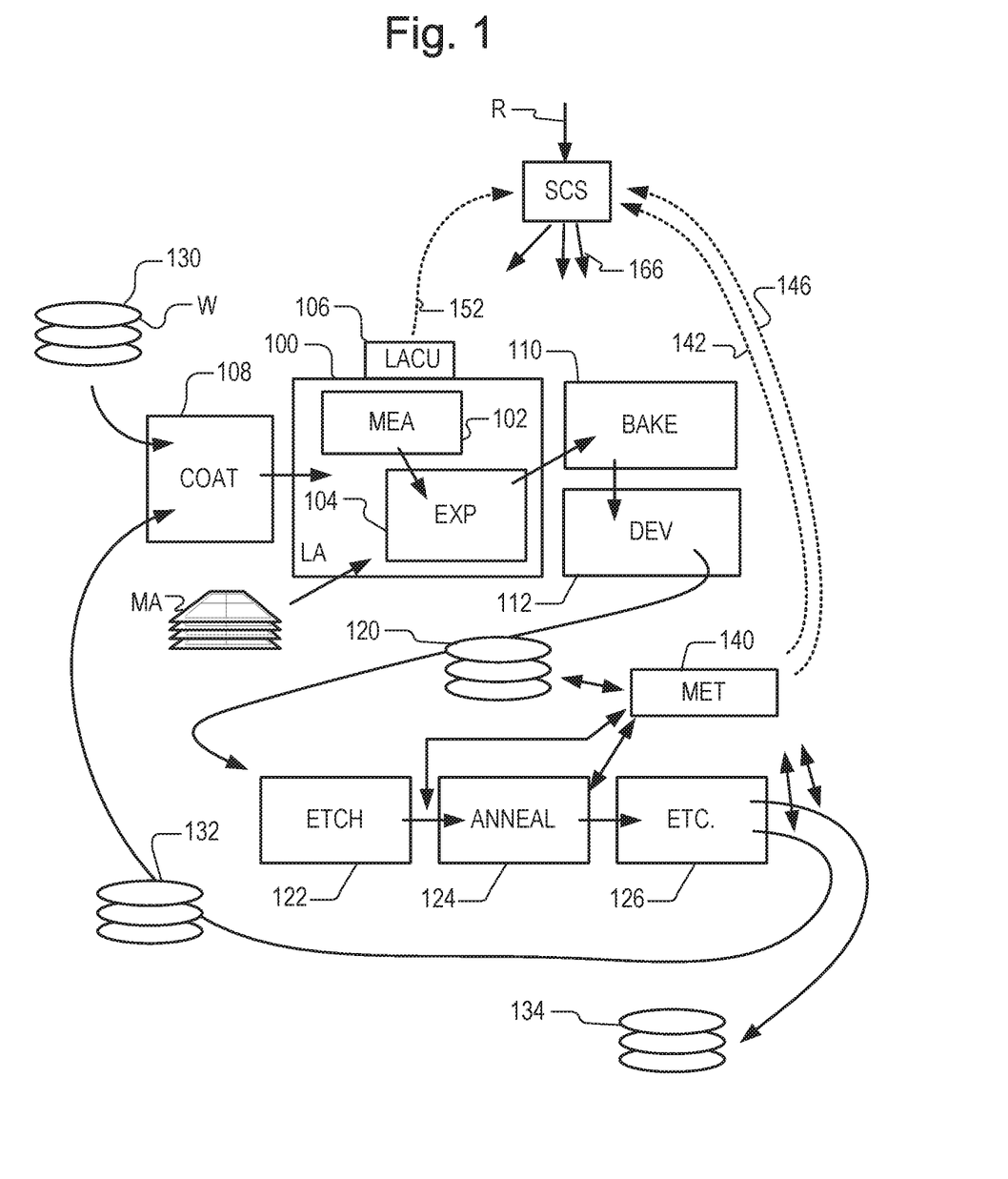
FIG. 1 depicts a lithographic apparatus together with other apparatuses forming a production facility for semiconductor devices.

FIG. 1 at 100 shows a lithographic apparatus LA as part of an industrial facility implementing a high-volume, lithographic manufacturing process. In the present example, the manufacturing process is adapted for the manufacture of semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 100 for short), a measurement station MEA is shown at 102 and an exposure station EXP is shown at 104. A control unit LACU is shown at 106. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU controls the movements and measurements of various actuators and sensors, causing the apparatus LA to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA for example is of a so-called dual stage type which has two substrate tables and two stations—an exposure station and a measurement station—between which the substrate tables can be exchanged.

Within the production facility, apparatus 100 forms part of a "litho cell" or "litho cluster" that contains also a coating apparatus 108 for applying photosensitive resist and other coatings to substrates W for patterning by the apparatus 100. At an output side of apparatus 100, a baking apparatus 110 and developing apparatus 112 are provided for developing the exposed pattern into a physical resist pattern. Between all of these apparatuses, substrate handling systems take care of supporting the substrates and transferring them from one piece of apparatus to the next. These apparatuses, which are often collectively referred to as the "track", are under the control of a track control unit which is itself controlled by a supervisory control system SCS, which also controls the lithographic apparatus via lithographic apparatus control unit LACU. Thus, the different apparatuses can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 120 are transferred to other processing apparatuses such as are illustrated at 122, 124, 126. A wide range of processing steps is implemented by various apparatuses in a typical manufacturing facility. For the sake of example, apparatus 122 in this embodiment is an etching station, and apparatus 124 performs a post-etch annealing step. Further physical and/or chemical processing steps are applied in further apparatuses, 126, etc. Numerous types of operation can be required to make a real device, such as deposition of material, modification of surface material characteristics (oxidation, doping, ion implantation etc.), chemical-mechanical polishing (CMP), and so forth. The apparatus 126 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 130 arriving at the litho cluster may be newly prepared substrates, or they may be substrates that have been processed previously in this cluster or in another apparatus entirely. Similarly, depending on the required processing, substrates 132 on leaving apparatus 126 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 126 used at each layer may be completely different in type. Further, even where the processing steps to be applied by the apparatus 126 are nominally the same, in a large facility, there may be several supposedly identical machines working in parallel to perform the step 126 on different substrates. Small differences in set-up, or faults between these machines can mean that they influence different substrates in different ways. Even steps that are relatively common to each layer, such as etching (apparatus 122) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system MET which receives some or all of the substrates W that have been processed in the litho cell. Metrology results are provided directly or indirectly to the supervisory control system (SCS) 138. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 140 which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 120 prior to etching in the apparatus 122. Using metrology apparatus 140, it may be determined, for example, that important performance parameters such as overlay or critical dimension (CD) do not meet specified accuracy requirements in the developed resist. Prior to the etching step, the opportunity exists to strip the developed resist and reprocess the substrates 120 through the litho cluster. As is also well known, the metrology results 142 from the apparatus 140 can be used to maintain accurate performance of the patterning operations in the litho cluster, by supervisory control system SCS and/or control unit LACU 106 making small adjustments over time, thereby minimizing the risk of products being made out-of-specification, and requiring re-work. Of course, metrology apparatus 140 and/or other metrology apparatuses (not shown) can be applied to measure properties of the processed substrates 132, 134, and incoming substrates 130.

Example Inspection Apparatus

Figure 2A:
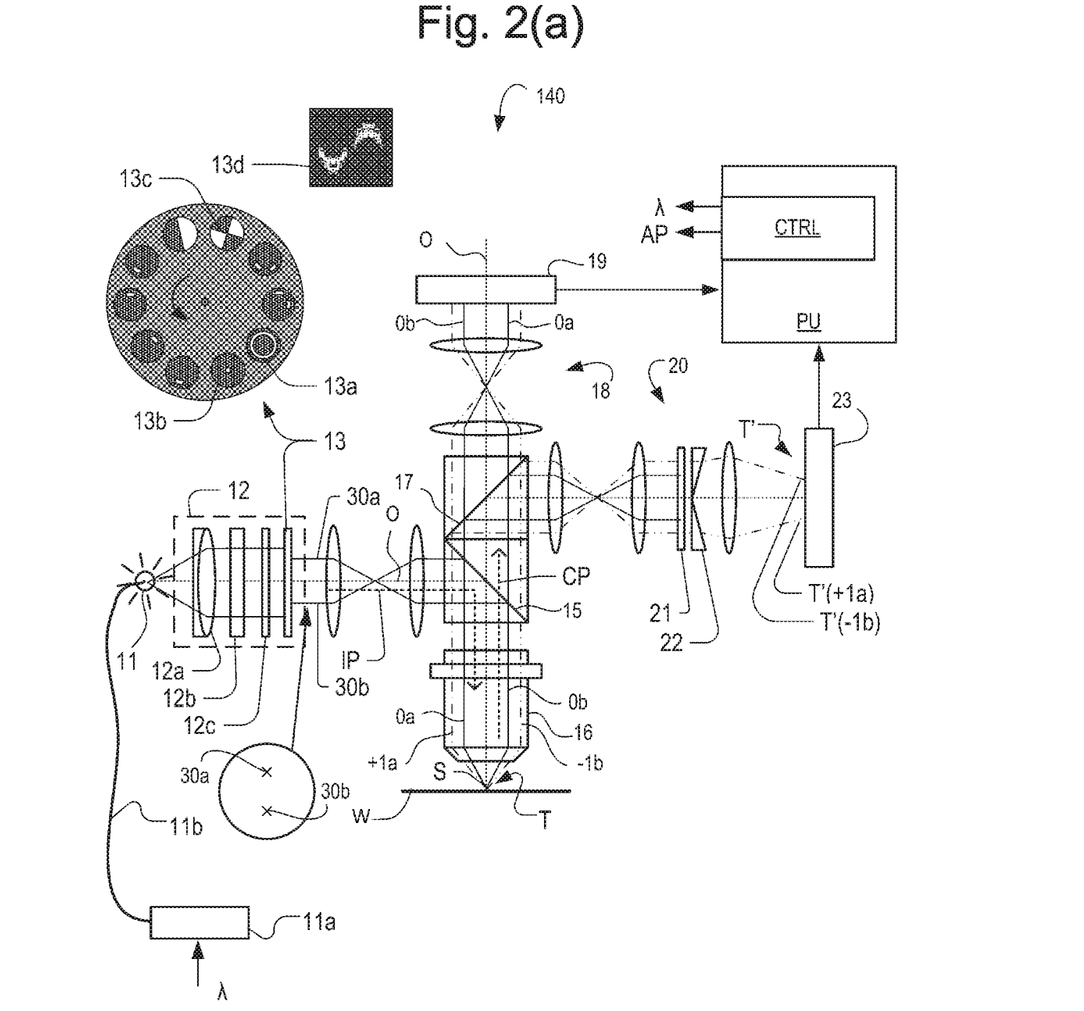
FIGS. 2(a)-2(b) illustrate schematically 2(a) an inspection apparatus adapted to perform angle-resolved scatterometry and dark-field imaging inspection methods in accordance with some embodiments of the invention and 2(b) an enlarged detail of the diffraction of incident radiation by a target grating in the apparatus of FIGS. 2(a)-2(b)

FIG. 2(a) shows schematically the key elements of an inspection apparatus implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 2(b).

As described in the prior applications cited in the introduction, the dark-field-imaging apparatus of FIG. 2(a) may be part of a multi-purpose angle-resolved scatterometer that may be used instead of, or in addition to, a spectroscopic scatterometer. In this type of inspection apparatus, radiation emitted by a radiation source 11 is conditioned by an illumination system 12. For example, illumination system 12 may include a collimating lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain numerical apertures over 1 if desired.

The objective lens 16 in this example serves also to collect radiation that has been scattered by the target. Schematically, a collection path CP is shown for this returning radiation. The multi-purpose scatterometer may have two or more measurement branches in the collection path. The illustrated example has a pupil imaging branch comprising pupil imaging optical system 18 and pupil image sensor 19. An imaging branch is also shown, which will be described in more detail below. Additionally, further optical systems and branches will be included in a practical apparatus, for example to collect reference radiation for intensity normalization, for coarse imaging of capture targets, for focusing and so forth. Details of these can be found in the prior publications mentioned above.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus. In the case of gratings, the structure is periodic. In the case of an overlay metrology target, the grating is printed on top of or interleaved with another grating that has been formed by a previous patterning step.

The various components of illumination system 12 can be adjustable to implement different metrology 'recipes' within the same apparatus. In addition to selecting wavelength (color) and polarization as characteristics of the illuminating radiation, illumination system 12 can be adjusted to implement different illumination profiles. The plane of aperture device 13 is conjugate with a pupil plane of objective lens 16 and the plane of the pupil image detector 19. Therefore, an illumination profile defined by aperture device 13 defines the angular distribution of light incident on substrate W in spot S. To implement different illumination profiles, an aperture device 13 can be provided in the illumination path. The aperture device may comprise different apertures 13a, 13b, 13c etc. mounted on a movable slide or wheel. It may alternatively comprise a fixed or programmable spatial light modulator (SLM). As a further alternative, optical fibers may be disposed at different locations in the illumination pupil plane and used selectively to deliver light or not deliver light at their respective locations. These variants are all discussed and exemplified in the documents cited above. The aperture device may be of a reflective form, rather than transmissive. For example, a reflective SLM might be used. Indeed, in an inspection apparatus working in the UV or EUV waveband most or all of the optical elements may be reflective.

Figure 2B:
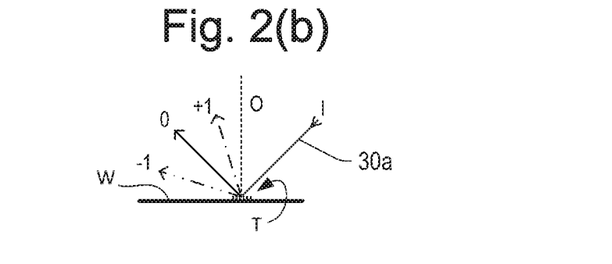

Depending on the illumination mode, example rays 30a may be provided so that the angle of incidence is as shown at 'I' in FIG. 2(b). The path of the zero order ray reflected by target T is labeled '0' (not to be confused with optical axis 'O'). Similarly, in the same illumination mode or in a second illumination mode, rays 30b can be provided, in which case the angles of incidence and reflection will be swapped compared with the first mode. In FIG. 2(a), the zero order rays of the first and second example illumination modes are labeled 0a and 0b respectively.

As shown in more detail in FIG. 2(b), target grating T as an example of a target structure is placed with substrate W normal to the optical axis O of objective lens 16. In the case of an off-axis illumination profile, a ray 30a of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

In the branch of the collection path for dark-field imaging, imaging optical system 20 forms an image T' of the target on the substrate W on sensor 23 (e.g. a CCD or CMOS sensor). An aperture stop 21 is provided in a plane in the imaging branch of the collection path CP which is conjugate to a pupil plane of objective lens 16. Aperture stop 21 may also be called a pupil stop. Aperture stop 21 can take different forms, just as the illumination aperture can take different forms. The aperture stop 21, in combination with the effective aperture of lens 16, determines what portion of the scattered radiation is used to produce the image on sensor 23. Typically, aperture stop 21 functions to block the zeroth order diffracted beam so that the image of the target formed on sensor 23 is formed only from the first order beam(s). In an example where both first order beams are combined to form an image, this would be the so-called dark field image, equivalent to dark-field microscopy.

The images captured by sensor 23 are output to image processor and controller PU, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose. Special designs of targets are provided to allow these measurements of different performance parameters to be made through the same basic asymmetry measurement method.

Referring again to FIG. 2(b) and the illuminating rays 30a, +1 order diffracted rays from the target grating will enter the objective lens 16 and contribute to the image recorded at sensor 23. Rays 30b are incident at an angle opposite to rays 30a, and so the −1 order diffracted rays enter the objective and contribute to the image. Aperture stop 21 blocks the zeroth order radiation when using off-axis illumination. As described in the prior publications, illumination modes can be defined with off-axis illumination in X and Y directions.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture stop 21 could be used to pass substantially only one first order of diffracted light to the sensor. In a further example, a pair of off-axis prisms 22 are used in combination with an on-axis illumination mode. These prisms have the effect of diverting the +1 and −1 orders to different locations on sensor 23 so that they can be detected and compared without the need for two sequential image capture steps. Effectively, separate images are formed at separated locations on the image sensor 23. In FIG. 2(a) for example, an image T'(+1a), made using +1 order diffraction from illuminating ray 30a, is spatially separated from an image T'(−1b) made using −1 order diffraction from illuminating ray 30b. This technique is disclosed in the above-mentioned published patent application US2011102753A1, the contents of which are hereby incorporated by reference. 2nd, 3rd and higher order beams (not shown in FIG. 2) can be used in measurements, instead of, or in addition to, the first order beams. As a further variation, the off-axis illumination mode can be kept constant, while the target itself is rotated 180 degrees beneath objective lens 16 to capture images using the opposite diffraction orders.

While a conventional lens-based imaging system is illustrated, the techniques disclosed herein can be applied equally with plenoptic cameras, and also with so-called "lensless" or "digital" imaging systems. There is therefore a large degree of design choice, which parts of the processing system for the diffracted radiation are implemented in the optical domain and which are implemented in the electronic and software domains.

Overlay Measurement

In a previous overlay measurement algorithm, which uses a single wavelength to acquire measurements, it is not possible from the measured signals to distinguish between the intensity asymmetry resulting from a change in overlay or a change in grating asymmetry. It has been proposed to address this problem by making measurements with multiple wavelengths and/or extending the target by adding bottom-grating pads (regions of the overlay target with no top grating so that the asymmetry in the bottom grating can be measured directly), multiple biases or pitches. However, such methods can either probe the wavelength sensitivity or differentiate the grating asymmetry, but do not both.

Bottom grating asymmetry measurements, that is measuring a part of the bottom grating over which no top grating is formed, can be used to correct overlay measurements for grating asymmetry. However, this requires additional area on the substrates to be dedicated to measurement targets and only calibrates the relationship between bottom grating asymmetry and overlay at recipe setup. Any change in this relation will result in an error in the correction.

Other previously proposed calibration methods rely on linear relations between measured asymmetries. As soon as additional terms come into play such methods are not reliable anymore.

Whilst calibration methods have been proposed for various different sources of error, the different methods collect there own measurement data, do not share results and apply separate corrections. This can result in some targets being measured multiple times to collect data for different purposes. This is inefficient in measurement time and usage of the available data. Thus, there is a need for an improved approach to measurement of the properties of a substrate, for example overlay.

Figure 5:
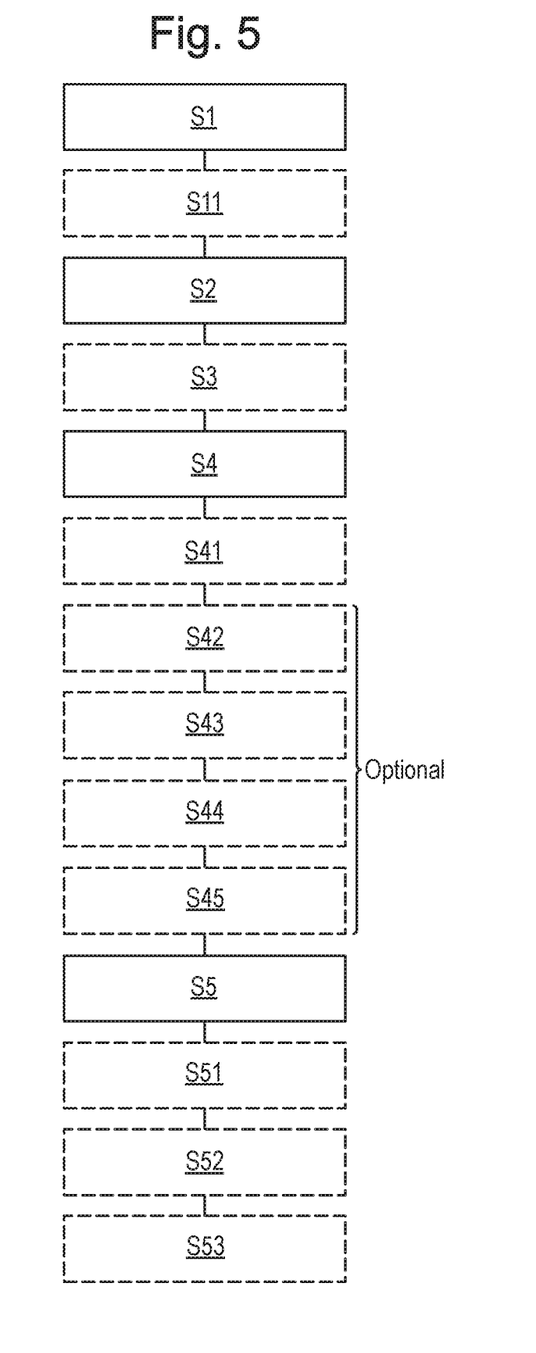
FIG. 5 depicts a measurement method according to an embodiment of the invention.

An embodiment of the invention will now be described with reference to overlay measurement by way of an example and with reference to FIG. 5.

A first step in an embodiment of the present invention is recipe setup S1, which includes design of a suitable target and selection S11 of suitable wavelengths to use for measurements.

Figure 3:
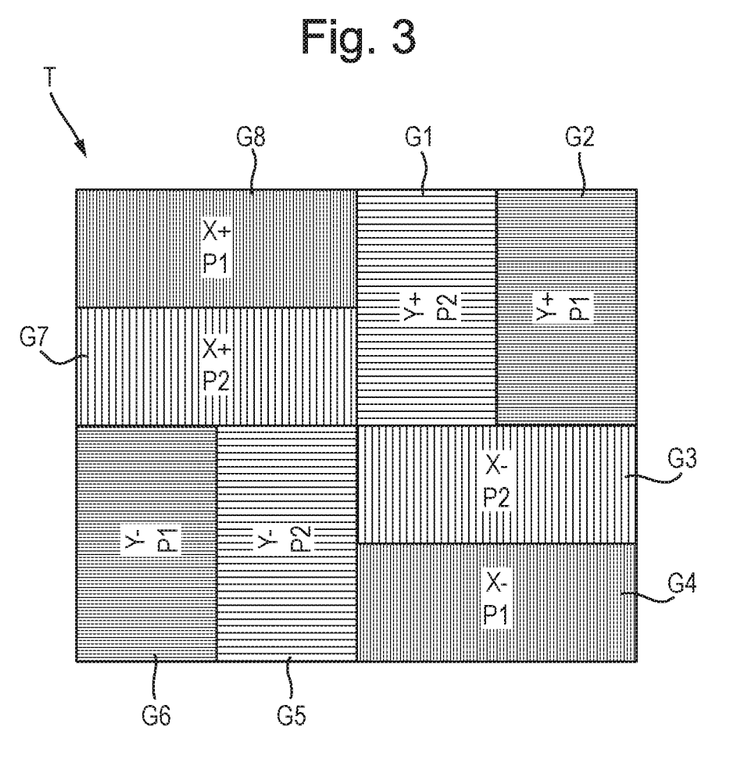
FIG. 3 depicts a target usable in a method of the invention.

A conventional overlay target comprises a bottom grating in a first layer of the substrate and a top grating, having the same pitch as the bottom grating, in a second layer of the substrate above the first layer. Often the top grating is positioned (if placed perfectly) with a predetermined offset, referred to as bias, relative to the bottom grating. A target may comprise two pairs of gratings with opposite biases, referred to as a bias-pair. An embodiment of the present invention can use an overlay target which consists of multiple pitches per layer-pair, with each pitch having its own bias-pair. A two-pitch target example T is shown in FIG. 3. This comprises sub targets G1 to G8 having grating lines oriented perpendicular to the X or Y directions, having pitches P1 or P2 and +ve or −ve biases, as indicated.

For this basic target structure an optimum overlay profile for a specific application is determined. For example, values for the pitches and the exact shapes and configurations of the gratings in the target can be chosen such that a single measurement with a specific condition—i.e. values for changeable settings of the metrology apparatus such as wavelength, polarization, aperture, ND-filter—can be used to collect all relevant intensities. Based on the recipe optimization, a relevant variation in wavelength can be determined which can probe the asymmetry variation due to wavelength differences without entering high sensitivity regions. A plurality of targets are provided on a substrate, often more than one per field or die. It is not necessary that all are identical. Some targets may have the same basic structure but differ in the exact values of the pitches and/or biases used. Other targets may have very different structures.

Figure 4:
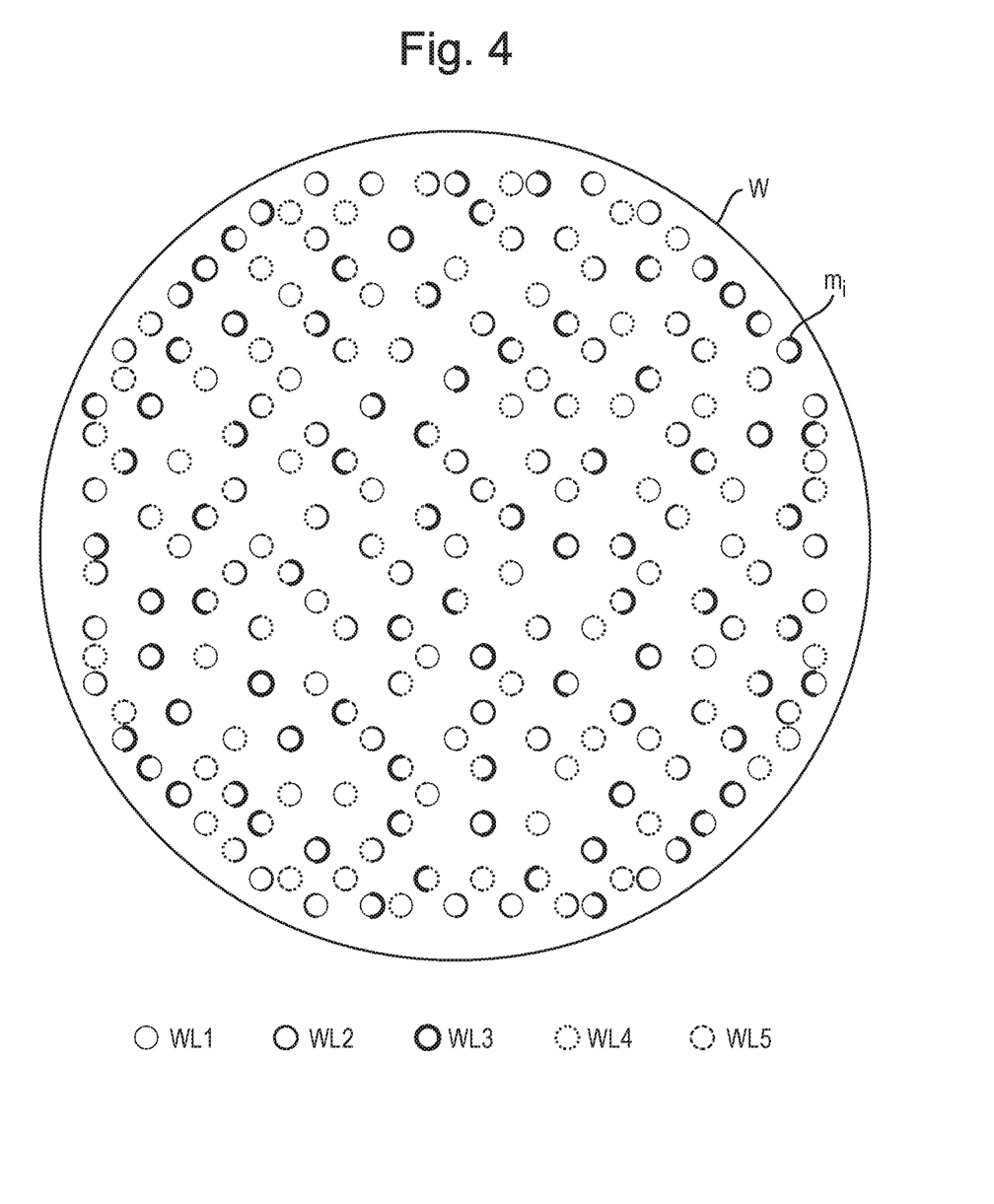
FIG. 4 depicts an exemplary measurement scheme used in an embodiment of the invention.

It is also desirable to devise a scheme for sampling the multiple targets on a substrate. In an embodiment, each target is sampled with a limited number of wavelengths, but over the substrates the wavelength is varied per target in such a way that an even coverage is achieved. FIG. 4 shows an example schemed in which 201 targets are measured using 5 wavelengths. Each measurement is represented by a circle $m_t$ where the line style of each half of the circle indicates one of the two wavelengths used to measure each target.

In an embodiment, the measurement system enables wavelength switching during the move from target to target so that there is no loss of throughput through use of multiple wavelengths and wavelength switching does not constrain the sampling pattern chosen. In an embodiment, the measurement system is configured to report the actual wavelength used for each measurement, for example using direct spectrometric measurement or indirect derivation based on a mechanical displacement of a component of the illumination system that affects the wavelength of the illumination radiation.

Having determined the sampling scheme, any necessary calibration measurement S2 are performed. Optionally, additional measurements S3 to determine any asymmetry in the sensor are performed, these are discussed further below.

In the production process, each substrate is measured S4 according to the devised scheme. A basic overlay measurement S41 of N targets is made together with additional optional measurements such as measuring the bottom grating array (BGA) S42; measuring the actual wavelength used per measurement S43; varying the wavelength used over the substrate; and/or measurements of a sensor or tool induced errors S45. For example, it is possible to apply correction methods to take into account the effects of asymmetries induced by the metrology tool in the final measured intensity. The optics of the metrology tool are not perfect, meaning that a ray might follow a slightly different optical path that its symmetrical, on pure geometrical considerations, counterpart. Such corrections are described in US patent application US 2016-0180517 A1, incorporated herein by reference in its entirety. In an embodiment, measurements needed to calculate correction are carried out only on a first substrate in a lot or batch, and then the corrections needed for other substrates are derived, thus removing the need to do such corrections on each substrate.

Once all desired measurements are obtained a fitting process S5 is performed. This includes sub-steps of determining correction factors S51, fitting S52 the measured asymmetries to the property of the substrate to be measured and outputting results S53. The processes are discussed further below.

The measured intensity asymmetry for each a target can be expressed as:

$$As_{b,w_t,n,p} = K_{w_m,n,p} \cdot (OV_n + d) + (Sp_{w_m,p} + dSp_{w_m,p} \cdot wl_n^e) \cdot Ap_{n,p} \quad (1)$$

With:
As (Asymmetry measured per bias, [gl]) per bias*wavelength*location*pitch [2*$w_t$*n*p]
K (Overlay Sensitivity, [gl/nm]), can be derived from As(+d)–As(–d) [$w_m$*n*p]
OV (Overlay) per target [n]
d (Bias)=±20 nm Ap (Asymmetry due to Process, [rad]) per location*pitch [n*p]
Sp (Sensitivity to Asymmetry Process, [gl/rad]) per wavelength*pitch [$w_m$*p]
dSp (Sensitivity to Asymmetry Process derivative to WL,[gl/(rad*nm)]) per wavelength*pitch [$w_m$*p]
wl□ (measured Wavelength set-error, [nm]) per target[n]
b=# bias per target (default: 2)
n=# locations measured on wafer
$w_t$=# wavelengths measured per target
$w_m$=# wavelengths measured over wafer ($w_m \geq w_t$)
p=# pitches per target The slope of the sensitivity, dSp, is the local slope due to wavelength set-error. It is determined per wavelength recipe setting, but covers the wavelength variation due to wavelength selection variations.

It should be noted that the sensitivities and asymmetries cannot be solved separately for different pitches, since they both are dependent on pitch. As a partial solution, $Ap_{n,p}$ can be split up in an location dependent asymmetry which is pitch independent ($Ap_n$) and a pitch (difference) dependent part ($Ap_{n,dp}$). In equation (1) the sensitivities (Sp, dSp) are determined for the complete substrate. For extension into intra-substrate components, additional position dependent parameters can be added to the equation. Furthermore, in some embodiments, terms other than the basic overlay dependence ($K_{n,p} \cdot (OV_n + d)$) can be omitted if not required.

Thus, the measurement values obtained from a substrate can be substituted into equation (1) to produce a plurality of equations to solve. These equations are simultaneous equations to the extent that one or more variables to be solved for are constrained to take the same value in two or more of the equations. However other variables may be allowed to take different values at different locations on the substrate of when measured by different wavelengths and are thus independent between different ones of the equations. There may be additional relationships or constraints between the variables to be solved for and these may make the per-target equations simultaneous.

As an initial step, half of the equations may be used for solving for K, so that the number of equations available for solving for the other variables is $w_t$*n*p and the number of unknowns is n+2*$w_m$*p+n*p.

Thus, possible solutions exist if one of the following conditions is met, in the example of using only two wavelengths to measure 100 targets.

| P | $w_t$ | lower limit @($w_m$ = 2, n = 100) |
|---|---|---|
| 1 | (2*n + 2*$w_m$)/n | $w_t$ > 2.04 (thus at least 3 wl) |
| >1 | | $w_t \geq 2$ |

Therefore it is possible to make a trade-off between target real-estate (single or multi-pitch) and acquisition time ($w_t$) and an appropriate compromise can be determined for a specific use of the invention. Measuring at different wavelengths over the whole substrate is not required, but will provide robustness for process variation and additional information in the relation between the sensitivities of the different wavelengths.

Additional Asymmetry-Terms and/or Sensitivities

Equation (1) has only limited asymmetry-terms and related sensitivity-terms. Both terms can be expanded to probe different disturbances or higher-order spatial models. The possible asymmetry terms that can be determined are a function of the number of wavelengths/target and the number of sensitivity-terms for a target containing two pitches.

For a two wavelength acquisition (with no variation over the substrate) up to 25 sensitivity parameters can be solved for a single asymmetry contribution. However, adding wavelength variation over the substrate reduces the number of options. For additional asymmetry-terms typically more wavelengths need to be measured per target.

Equation (1) can be extended to include Bottom Grating Asymmetry (BGA) measurement data. This enables an inline calibration of the relation between BGA and OV.

$$As_{b,w_t,n,p} = K_{w_m,n,p} \cdot (OV_n + d) + (Sp_{w_m,p} + dSp_{w_m,p} \cdot wl_n^e) \cdot Ap_{n,p} + Sb_{w_m,p} \cdot Ab_{n,p} \quad (1)$$

With:
- Ab (Asymmetry measured on BGA pad) per location*pitch [n*p]
- Sb (Sensitivity to Asymmetry BGA) per wavelength*pitch [w*p]

Equation 1 can also be extended to include algorithms to correct for the effects of asymmetries induced by the metrology tool, as discussed above. When combining all these corrections into one, the difference between calibration measurements and actual overlay measurements disappears: all data-points can be used as input for the correction. Any measurement with TIS and/or a target displacement can be taken into account to determine the relevant correction terms. This enables for instance the possibility to use the regular overlay measurements with an additional disturbances (e.g. random target displacement over the wafer) as input for a correction scheme for spot profile variations of the intensity in the illumination spot. Such a spot profile correction scheme corrects for the case of two or more gratings within 1 target, image of which are recorded in a single exposure. In this case the gratings necessarily do not have the same position within the illumination spot. During calibration the target is measured at different locations within the illumination spot. The derived intensity correction factors can be applied during measurement as a function of target position within the spot. Such a correction is described in more detail in US 2012-0242970 A1, which document is hereby incorporated by reference in its entirety.

If sufficient inputs are not available, the number of dimensions in the equations to be solved can be drastically reduced by introducing a model for the property of interest (e.g. overlay) as a function of position on the substrate. This means that the formerly independent variables become linked and it is possible to solve the equations only for the parameters of the model, instead of overlay per target location. Alternatively or in addition, specific terms in the equations can be replaced by model approximations. For example the term $Ap_{n,p}$, which represents asymmetry due to process per pitch and per target, can be replaced by a function representing asymmetry due to process in terms of parameters such as position, magnification and rotation.

If the complete wafer is measured, the asymmetry expression, equations (1) or (2), can be solved and the resulting overlay can be calculated per target.

A worked example of the equations that are solved in an embodiment of the invention is set out below.

Equation (1), repeated below, models measured asymmetry as a function of overlay process asymmetry and wavelength sensitivity of process asymmetry.

$$As_{b,w_t,n,p} = K_{w_m,n,p} \cdot (OV_n + d) + (Sp_{w_m,p} + dSp_{w_m,p} \cdot wl_n^e) \cdot Ap_{n,p}$$

As a example, a set of targets $T_1$ to $T_n$ having a single pitch is measured using wavelengths $WL_1$ to $WL_n$ to give the following equations:

$$As_{pb,WL1,T1} = K_{WL1,T1} \cdot (OV_{T1} + d) + (Sp_{WL1} + dSp_{WL1} \cdot wl_{T1}^{\varepsilon 1}) \cdot Ap_{T1}$$

$$As_{nb,WL1,T1} = K_{WL1,T1} \cdot (OV_{T1} - d) + (Sp_{WL1} + dSp_{WL1} \cdot wl_{T1}^{\varepsilon 1}) \cdot Ap_{T1}$$

$$As_{pb,WL2,T1} = K_{WL1,T1} \cdot (OV_{T1} + d) + (Sp_{WL2} + dSp_{WL2} \cdot wl_{T1}^{\varepsilon 2}) \cdot Ap_{T1}$$

$$As_{nb,WL2,T1} = K_{WL1,T1} \cdot (OV_{T1} - d) + (Sp_{WL2} + dSp_{WL2} \cdot wl_{T1}^{\varepsilon 2}) \cdot Ap_{T1}$$

(for all $w$ wavelengths) :

$$As_{pb,WLw,T1} = K_{WLw,T1} \cdot (OV_{T1} + d) + (Sp_{WLw} + dSp_{WLw} \cdot wl_{T1}^{\varepsilon w}) \cdot Ap_{T1}$$

$$As_{nb,WLw,T1} = K_{WLw,T1} \cdot (OV_{T1} - d) + (Sp_{WLw} + dSp_{WLw} \cdot wl_{T1}^{\varepsilon w}) \cdot Ap_{T1}$$

Target 2 $As_{pb,WL1,T2} = K_{WL1,T2} \cdot (OV_{T2} + d) + (Sp_{WL1} + dSp_{WL1} \cdot wl_{T2}^{\varepsilon 1}) \cdot Ap_{T2}$ $$As_{nb,WL1,T2} = K_{WL1,T2} \cdot (OV_{T2} - d) + (Sp_{WL1} + dSp_{WL1} \cdot wl_{T2}^{\varepsilon 1}) \cdot Ap_{T2}$$

(for $w$ wavelengths, for $n$ targets) :

$$As_{pb,WLw,Tn} = K_{WLw,Tn} \cdot (OV_{Tn} + d) + (Sp_{WLw} + dSp_{WLw} \cdot wl_{Tn}^{\varepsilon w}) \cdot Ap_{Tn}$$

$$As_{nb,WLw,Tn} = K_{WLw,Tn} \cdot (OV_{Tn} - d) + (Sp_{WLw} + dSp_{WLw} \cdot wl_{Tn}^{\varepsilon w}) \cdot Ap_{Tn}$$

Thus, the number of known variables is n*w (two biases are used to solve K) and the number of unknown variables is n+w+w+n. Therefore the equations are solvable provided the following condition is met:

$$n*w \leq 2n + 2w$$

i.e. $n \leq \dfrac{2w}{w-2}$ and therefore in this case more than two wavelengths are required.

Taking different wavelength sampling into account, if $w_t$ is the number of wavelengths measured per target and $w_m$ is the number of wavelengths measured across the whole substrate, then the following condition applies:

$$nw_t \leq 2n + 2w_m$$

$$n \leq \dfrac{2w_m}{w_t - 2}$$

Again, more than two wavelengths per target are required but adding more overall sampled wavelengths enables more targets to be measured.

Accordingly, the present invention can provide overlay asymmetry correction based on multiple pitch and wavelengths as well as overlay asymmetry correction for impact of wavelength set-error. Furthermore it enables sampling of multiple wavelengths over a substrate with limited impact on throughput. It is also possible to calibrate BGA to overlay relation for multiple wavelengths with limited impact on throughput. The single fit containing all asymmetry contributions and calibrations enables an elegant and numerically safer solution for all different contributions. With the invention, no prior knowledge is needed about the stack. All required information can be determined during a calibration phase suitable for recipe optimization, e.g. wavelength range. Further details of such a calibration are given in US 20160161864 A1, which document is hereby incorporated by reference in its entirety.

The method of the present invention can be applied directly during recipe-setup (no prior knowledge required) and can be used to select the best wavelength(s) during high volume manufacturing. The sampling of multiple wavelengths improves the robustness to process variation, especially for thicker stacks. A single pitch solution is possible (i.e. enabling use of a small target) at the cost of three wavelengths acquisitions per target.

The invention also enables a reduction in BGA correction error by adapting the relation between BGA and overlay on-the-fly (per lot, inter-wafer and intra-wafer)

With the invention, all measurements can be used for determining best calibration/correction and overlay results. There is no separation of data towards different tasks. Therefore, the invention provides the fastest collection of all relevant data.

The method of the invention is easily extendible towards more asymmetry contributions or model parameters (non-linear or higher order components).

The present invention can be applied using diffraction-based overlay scatterometers and also pupil-based scatterometers. The description above is based on diffraction-based overlay scatterometry but for pupil-based applications, the invention can be applied more easily. In pupil-based scatterometry more measurements are available (as function of NA-position). This provides possibilities to add asymmetry/sensitivity-terms at very limited cost. The invention can also be applied in diffraction-based focus scatterometry where different pitches can be also replaced by different target-designs (e.g. CD, duty-cycle, segmentation).

As noted above, for certain stacks and parts of the spectrum, measurement of overlay is highly sensitive to changes in the wavelength used for measurement. These particularly sensitive parts of the spectrum are avoided as much as possible during recipe-setup by examining the swing-curve response, but there is always a trade-off between robustness and sensitivity. However, often there is no wavelength available for which over the complete substrate the measured overlay results do not change significantly for small changes in wavelength of the measurement radiation. In known systems with a fixed wavelength but the potential for a systematic error in the actual wavelength compared to its nominal value, the resulting error will only show up on current systems as a tool-matching error, which is very difficult to investigate since there is no direct measurement of discrete filter characteristics possible in the tool. Similar effects due to wavelength changes occur for focus and CD scatterometry.

In some scatterometers, the actual wavelength and bandwidth of a measurement can be determined. This can be a direct measurement by the built-in spectrometer or a color-filter servo-based estimation of WL using the spectrometric calibration data. The WL error (dWL) and BW error (dBW) is defined as the difference between actual and set. After a complete substrate has been measured the WLerror and BWerror can be fitted with the measured overlay:

$$dOV = OV_{offset}(dWL) + OV_{slope}(dWL) + OV_{offset}(dBW) + OV_{slope}(dBW) + OV_{offset}(dWL*dBW) + OV_{slope}(dWL*dBW) \quad (3)$$

For both dWL and dBW an Offset and Slope term is fitted to correct for static shifts and sensitivity and the cross-term between both. The dOV can then be subtracted from the measured OV to remove the wavelength/bandwidth dependent part. For this method to perform best the wavelength distribution should be centered on its set-point. When the set-point is not included, extrapolation can be performed.

For a thick-stack it is known that the swing-curve will shift along the wavelength-axis due to (optical) stack height variations. This effect can be included by expanding the fit with position dependent linear (higher-order) terms. The effects systematic to change in WL/BW will corrected for, all other contributions to overlay (actual overlay, asymmetry, etc.) will be present in parameters of other models.

A similar correction can be derived for a focus scatterometer. This correction provides the following advantages:
reduced sensitivity to overlay or Focus swing-curve response
reduced sensitivity to color-filter variations (e.g. due to temperature)
reduction of tool-matching error due to WL/BW accuracy/precision
No additional measurement overhead required, correction can be done after measurement
All measurements are corrected in overlay or Focus to the same set-point for WL/BW.

The calculations to obtain measurements, and to control the selection of wavelengths and other recipe parameters, can be performed within the image processor and controller PU of the inspection apparatus. In alternative embodiments, the calculations of asymmetry and other parameters of interest can be performed remotely from the inspection apparatus hardware and controller PU. They may be performed for example in a processor within supervisory control system SCS, or in any computer apparatus that is arranged to receive the measurement data from the controller PU of the inspection apparatus. Control and processing of the calibration measurements can be performed in a processor separate from that which performs high-volume calculations using the correction values obtained. All of these options are a matter of choice for the implementer, and do not alter the principles applied or the benefits obtained.

While specific embodiments of the invention have been described above, it will be appreciated that the invention may be practiced otherwise than as described.

While the inspection apparatus or tool illustrated in the embodiments comprises a particular form of scatterometer having first and second branches for simultaneous imaging of pupil plane and substrate plane by parallel image sensors, alternative arrangements are possible. Rather than provide two branches permanently coupled to objective lens 16 with beam splitter 17, the branches could be coupled selectively by a movable optical element such as a mirror. The optical system could be made having a single image sensor, the optical path to the sensor being reconfigured by movable elements to serve as a pupil plane image sensor and then a substrate plane image sensor.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the inspection apparatus hardware and suitable periodic structures realized on substrates and patterning devices, an embodiment may include a computer program containing one or more sequences of machine-readable instructions implementing methods of measurement of the type illustrated above to obtain information about a lithographic process. This computer program may be executed, for example, within image processor and controller PU in the apparatus of FIG. 2 and/or the control unit LACU of FIG. 1. There may also be provided a data storage medium (e.g., semiconductor memory, magnetic or optical disk) having such a computer program stored therein.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 1-100 nm), as well as particle beams, such as ion beams or electron beams. Implementations of scatterometers and other inspection apparatus can be made in UV and EUV wavelengths using suitable sources, and the present disclosure is in no way limited to systems using IR and visible radiation.

The term "lens", where the context allows, may refer to any one or combination of various types of optical components, including refractive, reflective, magnetic, electromagnetic and electrostatic optical components. Reflective components are likely to be used in an apparatus operating in the UV and/or EUV ranges.

The breadth and scope of the present invention should not be limited by any of the above-described exemplary embodiments, but should be defined only in accordance with the following claims and their equivalents.

The invention claimed is:

1. A method of measuring a property of a substrate, the substrate having a plurality of targets formed thereon, the method comprising:
    performing Wt measurements of N targets of the plurality of targets using an optical measurement system that has at least one changeable setting, wherein obtaining the Wt measurements includes:
        setting the at least one changeable settings to a first setting;
        measuring a first value of a first one of the N targets at the first setting of the at least one changeable settings;
        measuring a second value of a second one of the N targets at the first setting of the at least one changeable settings;
        changing the at least one changeable settings to a second setting;
        measuring a third value of the first one of the N targets at the second setting of the at least one changeable settings;
        measuring a fourth value of the second one of the N targets at the second setting of the at least one changeable settings; and
    determining R property values of the N targets using plural Q equations and the total of N*Wt measurement values taken, where R<Q≤N*Wt.
2. The method of claim 1, wherein the Q equations are simultaneous equations.

3. The method of claim 1, wherein the total number Wm of different setting values of the changeable setting used across all N targets is greater than Wt.

4. The method of claim 1, wherein the optical measurement system is a scatterometer.

5. The method of claim 3, wherein the changeable setting is wavelength, bandwidth, aperture shape and/or polarisation of an illumination beam of the optical measurement system.

6. The method of claim 1, wherein the property is overlay between two pattern layers formed on the substrate.

7. The method of claim 1, wherein the target includes a grating.

8. The method of claim 7, wherein the target includes a plurality of gratings with different biases, orientations and/or pitches.

9. The method of claim 1, further comprising measuring the wavelength and/or bandwidth of an illumination beam of the optical measurement system at the time of each measurement and wherein each equation includes at least one term dependent on wavelength and/or bandwidth.

10. The method of claim 1, wherein the equations include terms correlating to at least one of:
    target asymmetry;
    bottom grating asymmetry;
    wavelength sensitivity of grating asymmetry;
    wavelength sensitivity of bottom grating asymmetry;
    sensor asymmetry; and
    illumination homogeneity.

11. The method of claim 1, wherein solving Q equations comprises obtaining a property value at the location of each of the N targets.

12. The method of claim 1, wherein solving Q equations comprises obtaining a function describing the property in terms of the property value across the substrate.

13. A device manufacturing method comprising:
    forming a first device layer on a substrate, the first device layer including a plurality of targets;
    measuring N targets of the plurality of targets using an optical measurement system, where N is an integer greater than 2 and each of the N targets is measured Wt times, where Wt is an integer greater than 2 so as to obtain N*Wt measurement values; and
    determining R property values using Q equations and the N*Wt measurement values, where R<Q≤N*Wt;
    making a decision about another process step;
    wherein the optical measurement system has at least one changeable setting and, for each of the N targets, measurement values are obtained using different setting values of at least one changeable setting; and
    making a decision is based on the R property values.

14. A non-transitory computer readable medium comprising processor readable instructions to cause an optical measurement system to perform a method of measuring a property of a substrate, the substrate having a plurality of targets formed thereon, the method comprising:
    performing Wt measurements of N targets of the plurality of targets using an optical measurement system that has at least one changeable setting, wherein obtaining the Wt measurements includes:
        setting the at least one changeable settings to a first setting;
        measuring a first value of a first one of the N targets at the first setting of the at least one changeable settings;

measuring a second value of a second one of the N targets at the first setting of the at least one changeable settings;

changing the at least one changeable settings to a second setting;

measuring a third value of the first one of the N targets at the second setting of the at least one changeable settings;

measuring a fourth value of the second one of the N targets at the second setting of the at least one changeable settings;

determining R property values of the N targets using plural Q equations and the total of N*Wt measurement values taken, where $R<Q \leq N*Wt$.

15. An inspection apparatus for measuring a property of a plurality of structures formed by a lithographic process on one or more substrates, the apparatus comprising an illumination optical system, a collection optical system and a processing system, the processing system being arranged to derive a measurement of the property of each structure at least partly from radiation collected by the collection optical system after being scattered by the structure under one or more sets of illumination conditions established by the illumination optical system, the processing system being configured to control the apparatus to derive a measurement of a property of a plurality of structures in the method of claim 1.

16. A lithographic system comprising:
    a lithographic apparatus comprising:
    an illumination optical system arranged to illuminate a pattern;
    a projection optical system arranged to project an image of the pattern onto a substrate; and
    an inspection apparatus as claimed in claim 15,
    wherein the lithographic apparatus is arranged to use the measurement results from the inspection apparatus, in applying the pattern to further substrates.

17. The method of claim 1, wherein a decision about a lithography process step is based on the R property values.

* * * * *